United States Patent [19]

Grabner et al.

[11] 4,264,739

[45] Apr. 28, 1981

[54] SPARGER FOR CELL CULTURE SYSTEM

[75] Inventors: Roy Grabner, Blue Bell; Edgar Scattergood, Lansdale; Miguel O. Villarejos, Norristown, all of Pa.

[73] Assignee: Merck & Co., Inc., Rahway, N.J.

[21] Appl. No.: 1,245

[22] Filed: Jan. 5, 1979

[51] Int. Cl.³ ............................................. C12N 5/02
[52] U.S. Cl. ..................................... 435/241; 435/309; 435/313; 435/818; 261/124
[58] Field of Search ................. 195/127, 139, 142; 261/122, 124; 435/313, 818, 309, 240, 241

[56] References Cited

U.S. PATENT DOCUMENTS

| | | | |
|---|---|---|---|
| 1,920,719 | 8/1933 | Stich | 195/142 |
| 1,959,554 | 5/1934 | Stich | 435/313 X |
| 2,305,796 | 12/1942 | Seidel | 195/142 X |
| 2,981,660 | 4/1961 | Achorn et al. | 195/142 |
| 3,035,702 | 5/1962 | Marvin | 210/169 |
| 3,407,120 | 10/1968 | Weiss et al. | 195/142 X |
| 3,424,433 | 1/1969 | Thayer | 261/123 |
| 3,711,072 | 1/1973 | Waldenville | 261/122 |
| 3,853,712 | 12/1974 | House et al. | 195/142 |
| 3,923,605 | 12/1975 | Gedde | 195/142 |
| 4,017,565 | 4/1977 | Muller | 195/142 X |
| 4,051,204 | 9/1977 | Muller et al. | 195/142 X |

OTHER PUBLICATIONS

Weiss et al., "Multisurface Tissue Propagator for Mass Scale Growth of Cell Monolayers" Biotechnology & Bioengineering, vol. X, pp. 601–615 (1968).

Taylor et al., "Evaluation of Dyna Cell Vessel for Production of Surface Substrate Dependent Cells" Biotechnology & Bioengineering, vol. XVII, pp. 1847–1852 (1975).

*Primary Examiner*—R. B. Penland
*Attorney, Agent, or Firm*—Donald J. Perrella; Hesna J. Pfeiffer

[57] ABSTRACT

A sparger for mass cell culture systems is formed from an elongated tube having a plurality of ports.

9 Claims, 1 Drawing Figure

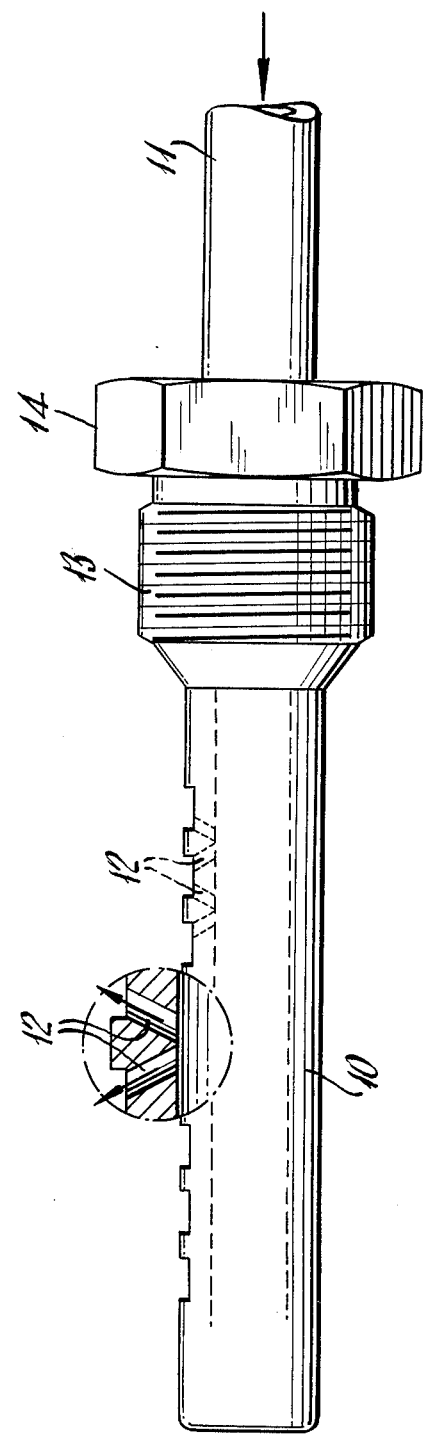

SPARGER FOR CELL CULTURE SYSTEM

BACKGROUND OF THE INVENTION

Human and animal vaccines have been commercially produced by growing the desired virus in primary cells. The initial commercial processes involved the use of large quantities of individual bottles having cells growing on the inner surface of the bottles. As production techniques evolved, the original bottles were replaced by roller bottles which somewhat reduced the number of bottles required and the handling problems associated therewith.

More recent mass cell culture systems involve the multi-plate unit disclosed in U.S. Pat. No. 3,407,120 and the Biotec cylindrical rotating disc apparatus. In all mass cell culture systems, however, it is a requirement that the cells be aerated. It has become commonplace to aerate the system with a mixture of air and $CO_2$ thereby aerating the system and controlling pH at the same time. Typically, a mixture of 95% air and 5% $CO_2$ is used. Due to the large area involved in mass cell culture systems, it is nevertheless difficult to achieve the desired pH control.

OBJECTS OF THE INVENTION

It is, accordingly, an object of the present invention to provide a mass cell culture system wherein pH control is readily and easily effected. Another object is to provide an improved sparger for aerating a mass cell culture system. A further object is to provide an improved method for aerating a mass cell culture system and for controlling pH. Yet another object is to provide the yields in mass cell culture systems. These and other objects of the present invention will be apparent from the following description.

SUMMARY OF THE INVENTION

Improved aeration, pH control and increased yield in mass cell culture systems are obtained by aerating the system with a sparger formed of an elongated tube having a plurality of ports.

BRIEF DESCRIPTION OF THE DRAWING

FIG. 1 is a side elevation view of a sparger according to the present invention.

DETAILED DESCRIPTION

The present invention relates to mass cell culture systems and, more particularly, to a sparger for a mass cell culture system.

It has now been found that improved aeration, pH control and increased yield in mass cell culture systems are obtained by aerating the system with a sparger formed of an elongated tube having a plurality of ports.

As shown in FIG. 1 the sparger of the present invention comprises a tube 10 having inlet means 11 at one end and sealed at the other end. Located adjacent to the sealed end are a plurality of small outlet ports or vents having a diameter of from about 0.04 cm to about 0.14 cm, typically about 0.09 cm. Tube 10 has a thickened threaded section 13 adapted to screw into a complementarily threaded section of the cell culture apparatus. A lock nut 14 secures tube 10 to the cell culture apparatus.

The encircled portion of FIG. 1 is an enlarged detail of two ports. As shown the ports 12 are perforations in the sidewall of tube 10. As shown the ports may be angular with respect to a line perpendicular to the longitudinal axis of tube 10, but need not be angular.

The following examples illustrate the present invention without, however, limiting the same thereto.

EXAMPLE 1 (Comparative)

A multi-plate propagator of the type described in U.S. Pat. No. 3,407,120 having a volume of 70 liters and equipped with a sparger having a single gas outlet is planted with a cell suspension prepared from 285 11.5 day-old chick embryos. The propagator is kept vertical (plates horizontal) with plates rotating at 1/6 rpm throughout the growth phase. A sparge of $CO_2$ (0.5%) in air is provided at a rate of 400 ml/minute. After 72 hours the attached cells are harvested from the plates using a trypsin solution and $42 \times 10^9$ cells are obtained.

EXAMPLE 2 (Comparative)

The procedure of Example 1 is repeated with a yield of $39 \times 10^9$ cells.

EXAMPLE 3

The procedure of Example 1 is repeated except substituting a sparger according to the present invention. The yield of cells is $48 \times 10^9$, an increase in yield of 14% with respect to Example 1 and 23% with respect to Example 2.

What is claimed is:

1. In a gas sparger for a mass cell culture system, the improvement wherein the sparger comprises an elongated tube open at one end and sealed at the other end, the open end comprising a gas inlet means, the elongated tube having a plurality of indentations along its longitudinal axis, each indentation alternating with an unindented area of the elongated tube thereby providing the appearance of merlons, and two gas outlet channels originating beneath each unindented area and passing through the wall of the elongated tube wherein one of the two gas outlet channels passes angularly to the intended area on one side of the unindented area beneath which it orginates, and the other of the two gas outlet channels passes angularly to the indented area on the other side of the unindented area beneath which it originates thereby forming an angle between the two channels which is substantially V-shaped.

2. A sparger according to claim 1 wherein the outlet ports have a diameter of from about 0.04 cm to about 0.14 cm.

3. A sparger according to claim 2 wherein the outlet ports have a diameter of about 0.09 cm.

4. A sparger according to claim 1 wherein the elongated tube containing the plurality of outlet ports has a threaded section adapted to be screwed into a threaded opening in the wall of the mass cell culture system.

5. A sparger according to claim 1 wherein some of the channels form an acute angle and some of the channels form an obtuse angle with the longitudinal axis of the tube.

6. A sparger according to claim 1 wherein the angles which each channel forms with the longitudinal axis of the tube are alternately acute and obtuse.

7. A method for aerating a mass cell culture system comprising passing the aerating gas to a sparger according to claim 1 and forcing the gas along the longitudinal axis of the tube and through the outlet channels.

8. A method according to claim 7 wherein the outlet ports have a diameter of from about 0.04 cm to about 0.14 cm.

9. A method according to claim 7 wherein the outlet ports have a diameter of about 0.09 cm.

* * * * *